United States Patent
Kida et al.

(10) Patent No.: US 10,617,705 B1
(45) Date of Patent: Apr. 14, 2020

(54) ISOQUERCITRIN COMPOSITIONS

(71) Applicant: ALPS Pharmaceutical Ind. Co. Ltd., Gifu (JP)

(72) Inventors: Hiroaki Kida, Gifu (JP); Naoto Yamaguchi, Gifu (JP); Mitsunori Ono, Nagano (JP)

(73) Assignee: Alps Pharmaceutical Ind. Co., Ltd., Gifu (JP)

( * ) Notice: Subject to any disclaimer, the term of this patent is extended or adjusted under 35 U.S.C. 154(b) by 0 days.

(21) Appl. No.: 16/582,730

(22) Filed: Sep. 25, 2019

Related U.S. Application Data

(60) Provisional application No. 62/796,126, filed on Jan. 24, 2019.

(51) Int. Cl.
*A61K 31/7048* (2006.01)
*A61K 9/48* (2006.01)

(52) U.S. Cl.
CPC ........ *A61K 31/7048* (2013.01); *A61K 9/4858* (2013.01)

(58) Field of Classification Search
CPC .......................... A61K 31/7048; A61K 9/4858
See application file for complete search history.

(56) References Cited

U.S. PATENT DOCUMENTS

| 4,285,964 | A | 8/1981 | Niebes et al. |
| 9,844,595 | B2 | 12/2017 | Niebes et al. |
| 2008/0187622 | A1 | 8/2008 | Moriwaki et al. |
| 2016/0095923 | A1 | 4/2016 | Niebes et al. |

FOREIGN PATENT DOCUMENTS

EP  1967187 B1  4/2011

OTHER PUBLICATIONS

Akiyama et al "Constituents of Enzymatically Modified Isoquercitrin and Enzymatically Modified Rutin (Extract)" Journal of the Food Hygiene Society of Japan vol. 41, pp. 54-60, 2000.
Flaumenhaft et al "Therapeutic Implications of Protein Disulfide Isomerase Inhibition in Thrombotic Disease" Arteriosclerosis, Thrombosis, and Vascular Biology vol. 35, pp. 16-23, 2015.
Murota et al "α-Oligoglucosylation of a Sugar Moiety Enhances the Bioavailability of Quercetin Glucosides in Humans" Archives of Biochemistry and Biophysics vol. 501, pp. 91-97, 2010.
Stopa et al "Protein Disulfide Isomerase Inhibition Blocks Thrombin Generation in Humans by Interfering with Platelet Factor V Activation" Journal of Clinical Investigation Insight vol. 2, pp. 1-13, 2017.
Zwicker "Cancer Associated Thrombosis and Isoquercetin (CAT IQ) (CAT IQ)" ClinicalTrials.gov Identifier: NCT02195232.

*Primary Examiner* — Jonathan S Lau
(74) *Attorney, Agent, or Firm* — Cesari and McKenna, LLP

(57) ABSTRACT

A water-soluble pharmaceutical composition containing isoquercitrin, L-arginine, and ascorbic acid or an alkali salt thereof, in which the molar ratio between the isoquercitrin, L-arginine, and the ascorbic acid or alkali salt is 1:1.6-2.6: 0.16-1.95.

20 Claims, 1 Drawing Sheet

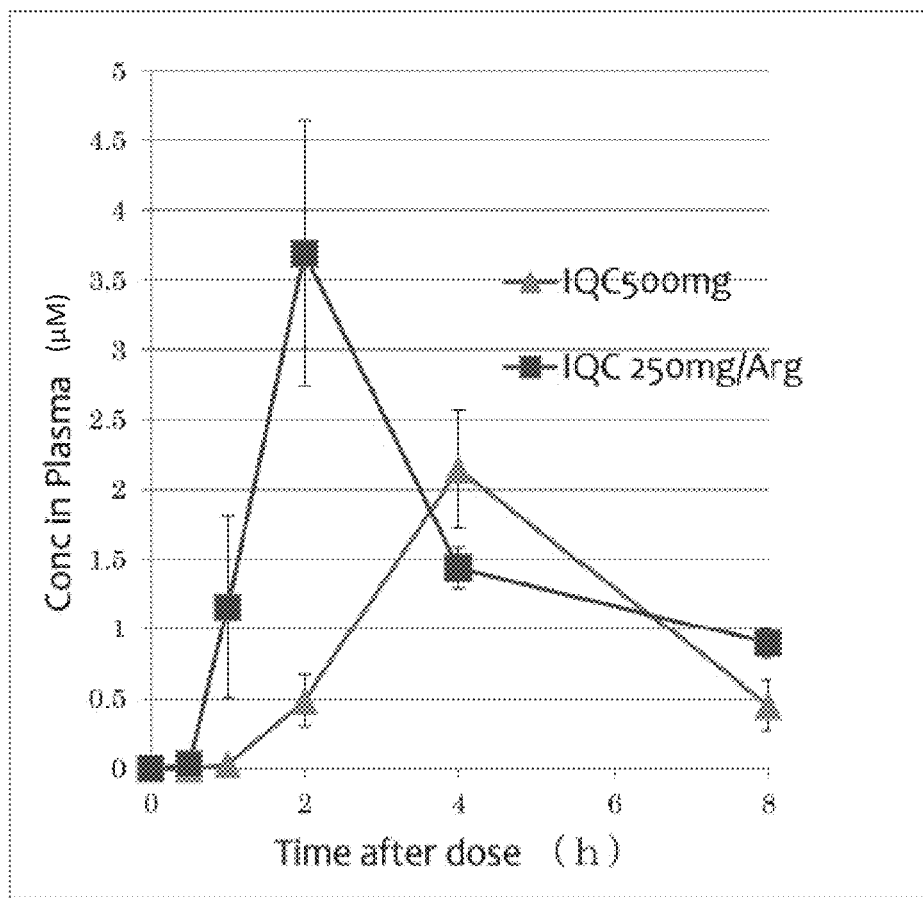

ISOQUERCITRIN COMPOSITIONS

CROSS-REFERENCE TO RELATED APPLICATIONS

This application claims the benefit of U.S. Provisional Application No. 62/796,126, filed on Jan. 24, 2019. The content of the prior application is hereby incorporated by reference in its entirety.

BACKGROUND

Isoquercitrin is the 3-O-glucoside of quercetin and several unexpected bioactivities have been ascribed to it. For example, it has been reported that isoquercitrin can inhibit protein disulfide isomerase (PDI), an enzyme strongly implicated in thrombus formation. See Flaumenhaft et al., Arteriosclerosis, Thrombosis, and Vasc. Biol., 2015, 35:16-23. It is believed that inhibitors of PDI, e.g., isoquercitrin, can prevent or block thrombosis.

A Phase II/III clinical trial is ongoing to test the ability of isoquercitrin to inhibit is cancer-associated thrombosis. See the CAT IQ trial on the world wide web at clinicaltrials.gov. It is noteworthy that the daily doses of isoquercitrin administered in the trial are 500 mg and 1000 mg. These doses are unusually high, as compared to the doses of typical pharmaceuticals. It is likely that a large dose of isoquercitrin is required to achieve sufficient bioavailability, due to its relatively low oral absorption.

Enzymatically modified isoquercitrin (EMIQ) with higher water solubility has been developed to improve the bioavailability of isoquercitrin. See Murota et al., Arch. Biochem. Biophys., 2010, 501:91-97. Yet, EMIQ is a mixture of at least five bioactive isoquercitrin derivatives. See Akiyama et al., J. Food Hyg. Soc. Japan, 1999, 41:54-60. It is impractical to use such a mixture of active ingredients as a drug in humans according to present US Federal Drug Administration guidelines.

There is a need to develop pharmaceutical compositions with higher oral absorption of isoquercitrin via improved water solubility without the above-described drawbacks.

SUMMARY

To address the above need, a water-soluble pharmaceutical composition is provided that contains isoquercitrin, L-arginine, and an alkali salt of ascorbic acid. In the composition, the molar ratio between the isoquercitrin, L-arginine, and the alkali salt of ascorbic acid is 1:1.6-2.6:0.16-1.95.

The details of the invention are set forth in the description below. Other features, objects, and advantages of the invention will be apparent from the detailed description, the drawing, and also from the appended claims.

BRIEF DESCRIPTION OF THE DRAWING

FIG. 1 is a plot of plasma concentration versus time after administration of 500 mg isoquercitrin (IQC 500 mg) and 250 mg isoquercitrin as isoquercitrin/L-arginine (IQC 250 mg/Arg).

DETAILED DESCRIPTION

As mentioned above, a water-soluble composition is disclosed herein that contains L-arginine, isoquercitrin, and an ascorbic acid alkali salt. The molar ratio between these three components is 1:1.6-2.6:0.16-1.95, preferably, 1:1.8-2.5:0.36-1.25. An exemplary water-soluble composition contains isoquercitrin, L-arginine, and an alkali salt of ascorbic acid at a molar ratio of 1:2.3:0.42.

Notably, the alkali salt of ascorbic acid can be a sodium salt or a potassium salt. In a particular composition, the alkali salt is a sodium salt.

The water-soluble pharmaceutical composition can also include vitamin B1, vitamin B3, vitamin B6, vitamin B9, or vitamin B12, in addition to isoquercitrin, L-arginine, and an alkali salt of ascorbic acid. The molar ratio of isoquercitrin to each water soluble vitamin in the composition can be 1:0.01-0.1.

The water-soluble pharmaceutical composition can be formulated for oral administration or for topical administration. For example, the composition for oral administration can be a liquid, a capsule, a tablet, a pill, or a gel. If formulated for topical administration, the composition can be a solution, a liniment, a lotion, a cream, an ointment, a paste, a gel, or an emulgel.

The water-soluble compositions of isoquercitrin, L-arginine, and alkali salt of ascorbic acid described above can be produced by the methods set forth in U.S. Patent Application Nos. 62/661,255 and 62/720,651, the contents of which are incorporated herein in their entireties.

In the water-soluble composition, isoquercitrin is typically present in a content of 10 wt % or higher (e.g., 20 wt % or higher, 30 wt % or higher, and 50 wt % or higher). L-arginine is also present at 10 wt % or higher (e.g., 20 wt % or higher, 30 wt % or higher, and 50 wt % or higher). The alkali salt of ascorbic acid is present at 2 wt % or higher (e.g., 4 wt % or higher, 6 wt % or higher, and 10 wt % or higher).

The isoquercitrin can be in a hydrate form or an anhydrous form. Similarly, the L-arginine also can be in a hydrate form or an anhydrous form.

The water-soluble composition, either a solid form or an aqueous form, can be in varied formulations for pharmaceutical, medical, or cosmetic use.

In one embodiment, the composition is in an oral formulation, e.g., a liquid, a capsule, a tablet, a pill, and a gel. An exemplary composition is in a capsule or a tablet, each formed from enteric coating. The composition can further contain a pharmaceutically active agent, a pharmaceutically acceptable excipient, or a combination thereof. This embodiment includes a composition that is a pharmaceutical drug, a dietary supplement, a natural health product, a cosmetic product, a food product, or a beverage.

In another embodiment, the composition is in a topical formulation, e.g., one of a solution, a liniment, a lotion, a cream, an ointment, a paste, a gel, and an emulgel. The composition can further contain a pharmaceutically active agent, a topically acceptable excipient, or a combination thereof. This embodiment includes a composition that is a cosmetic product, a skin care product, or a pharmaceutical drug.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. The publications cited herein are incorporated by reference in their entirety.

Example 1: Preparation of Isoquercitrin/L-arginine Samples

An exemplary isoquercitrin/L-arginine mixture was prepared by mixing 0.01 mol isoquercitrin with an aqueous solution containing 0.02 mol L-arginine, heating the mixture to 80° C. until the isoquercitrin dissolved completely, and adding 0.001 mol sodium ascorbate. After cooling, the stability of isoquercitrin was tested by heating the mixture to 50° C. and quantifying by HPLC the amount of intact isoquercitrin remaining after 0 h, 5 h, and 24 h. The results showed that the amount of intact isoquercitrin at 5 h and 24 h at 50° C. was 100% and 98.1%, respectively, of the initial amount of isoquercitrin in the solution. A similar study was performed to assess the stability of a flavonoid related to isoquercitrin, i.e., catechin, after dissolving it with L-arginine and sodium ascorbate. The amount of intact catechin remaining in the solution after 5 h and 24 h at 50° C. was 30.8% and 2.3%, respectively. It was quite unexpected that only 1.9% of the isoquercitrin degraded after 24 h, as compared to 97.7% of the catechin under identical conditions.

A second exemplary isoquercitrin/L-arginine mixture was prepared by first dissolving 105.5 g of L-arginine (0.61 mol) in 845 ml $H_2O$ heated to 45° C., then adding 20.9 g of L-ascorbic acid sodium salt (0.11 mol) and 46.5 g of hydrogenated polydextrin and stirring until fully dissolved.

To the above solution, 127 g of isoquercitrin monohydrate (0.26 mol) was added and the resulting mixture was heated at 80° C. for 30 min. Upon complete dissolution of the isoquercitrin, the solution was spray dried and sieved at 80 mesh. Any remaining $H_2O$ was evaporated in vacuo to leave a viscous oil, followed by vacuum drying at 60° C. for 8 hours to provide a yellow orange solid composition (253.9 g).

Example 2: Capsule Formulation Preparation

Formulations of isoquercitrin and isoquercitrin/L-arginine were prepared with the components shown in Table 1 below. For dissolution studies, the formulations were used as is. For clinical studies, the formulations were encapsulated in size #1 acid resistant delayed release hypromellose capsules (DRcaps™) manufactured by Capsugel.

TABLE 1

Formulation contents

| Ingredient | Formulation 1 | Formulation 2 | Formulation 3 |
|---|---|---|---|
| isoquercitrin (mg)/(w/w %) | 250/77.9 | 125/32.2 | 62.5/19.9 |
| L-arginine (%) | | 26.7% | 16.6% |
| ascorbic acid Na salt (w/w %) | | 5.3% | 3.2% |
| dextrin (w/w %) | 15.8% | 11.8% | 7.3% |
| crystalline cellulose (w/w %) | | 19.0% | 46.7% |
| glycerin fatty acid ester (w/w %) | 6.3% | 5.0% | 6.3% |
| Total (w/w %) | 100% | 100% | 100% |

Example 3: Solubility Test

The ability of isoquercitrin to dissolve in $H_2O$ from Formulation 1 and Formulation 2 were measured as follows. An amount of Formulation 1 containing 500 mg of isoquercitrin and an amount of Formulation 2 containing 250 mg isoquercitrin were each added to separate 25 mL of distilled $H_2O$ water and agitated for 30 s. After an aliquot was removed (0 min.), each mixture was heated at 37° C. with slow agitation. Aliquots were collected from each mixture at 5 min. and 30 min. after heat treatment began. Each aliquot was passed through a 0.45 μm filter and the isoquercitrin concentration in the filtrate measured by HPLC. The results are shown below in Table 2.

TABLE 2

Water solubility of isoquercitrin

| Incubation time | Formulation 1 | Formulation 2 | Fold difference |
|---|---|---|---|
| 0 min. | 0.02 mg/ml | 7.9 mg/ml | 395 |
| 5 min. | 0.06 mg/ml | 9.9 mg/ml | 165 |
| 30 min. | 0.07 mg/ml | 9.8 mg/ml | 140 |

The results show that the amount of isoquercitrin dissolving from Formulation 2, i.e., isoquercitrin/L-arginine/ascorbate, was 140 to 395-fold greater than the amount of isoquercitrin dissolving from Formulation I, which is free of L-arginine and ascorbate. Clearly, Formulation 2 contains significantly more soluble isoquercitrin, as compared to Formulation 1.

Example 4 Permeation Study in Caco-2 Cells

Permeation of a drug into cultured intestinal Caco-2 cells is measured to predict the relative absorption rate of the drug when given orally.

Formulations 1 and 2 described above in Example 2 were added separately into a solution. A 500 μL aliquot of each sample was added to the apical side of Caco-2 cells that had been cultured for 19 days, and 2,000 μL of HBSS buffer was placed on the basolateral side of the cells. The cells were cultured in an incubator for 2 hours at 37° C., after which media was recovered from both the apical and basolateral sides of the cells. The concentration of isoquercitrin in the media was determined by HPLC, and the degree of absorption from the apical side to the basolateral side was determined by the following equation:

$$\text{Permeation rate (\%)} = \frac{\text{Permeation amount of basolateral side (nM)}}{\text{Loaded amount of apical side (nM)}} \times 100$$

The results showed that Formulation 1, which contained isoquercitrin but lacked L-arginine and ascorbate, had a permeation rate of 0.008%, while Formulation 2, which contained isoquercitrin, L-arginine, and ascorbate, exhibited a remarkable 37-fold increase in permeation (absorption) rate to 0.298%.

Example 5: Clinical Pharmacokinetic Study

A randomized clinical pharmacokinetic study was performed to compare the three different isoquercitrin formulations described above in Example 2 administered in a single dose to 10 volunteers under fasting conditions. Healthy males between the ages of 24 and 39 years inclusive having body mass index values within the range of 19.6-24.3 participated in the study.

Capsules containing formulations 1-3 shown in Table 1 were prepared as described above. Each volunteer took two capsules containing (i) formulation 1 (IQC; 500 mg isoquercitrin total), (ii) formulation 2 (IQC/Arg; 250 mg isoquercitrin total), or (iii) formulation 3 (IQC/Arg; 125 mg isoquercitrin total) on three test days, administered according to a previously randomized sequence.

Isoquercitrin levels were measured in blood samples removed from the participants before dosing (0 h) and 0.5, 1, 2, 4, and 8 h after dosing following established procedures. More specifically, in order to determine isoquercitrin levels, plasma prepared from each blood sample was treated first to deconjugate isoquercitrin metabolites into aglycones quercetin and isorhamnetin, which were subsequently quantified by HPLC.

Briefly, 200 μl plasma samples were mixed with 10 μl 10% dithiothreitol and 50 μl 0.58 mol/L acetic acid. The mixture was treated with 1000 U of beta-glucuronidase and 100 U/mL of sulfatase, both from *Helix pomatia* Type HP-2, in 0.1 M sodium acetate buffer (pH 5.0) for 120 min at 37° C.

After deconjugation, 500 μl of 10 mM oxalic acid was added to each sample and the mixture centrifuged at 10,000×g for 5 min. All treated samples were subjected to solid phase extraction using preconditioned Oasis HLB cartridges as directed by the manufacturer (Waters, Milford Mass. USA). The extracted eluates were evaporated under nitrogen, reconstituted in methanol, and subjected to HPLC analysis by loading each eluate on a C18 column (Waters ACQUITY UPLC BEH; 1.7 μm, 2.1×100 mm), applying a gradient solvent system of 0.1% formic acid in $H_2$/0.1% formic acid in acetonitrile HPLC, and detecting the presence of quercetin and isorhamnetin with an Ultimate 3000 rapid separation LC, Q Exactive spectrometer. The concentration of each aglycone was calculated using a standard curve prepared with authentic quercetin and isorhamnetin internal standards. The analytical limit for quercetin and isorhamnetin under the above conditions was 0.03 μM at 4° C.

Pharmacokinetic profiles are shown in FIG. 1. Of note, administering IQC/Arg 125 mg resulted in a pharmacokinetic profile similar to that of IQC/Arg 250 mg but with the values of $C_{max}$ and AUC about half those seen with the higher dose, indicative of a dose-dependent relationship.

Pharmacokinetic values calculated from profiles similar to those depicted in FIG. 1 are shown in Table 3 below.

TABLE 3

Pharmacokinetics

| Parameters | Treatment | | |
|---|---|---|---|
| | IQC 500 mg | IQC/Arg 250 mg | IQC/Arg 125 mg |
| AUC (μmol · hr/L) (0-8 h) | 8.1 ± 1.7 | 12.5 ± 1.7 | 4.5 ± 0.9 |
| $C_{max}$ (μM) | 2.2 ± 0.4 | 4.2 ± 1.0 | 1.2 ± 0.3 |
| $T_{max}$ (hr) | 3.8 ± 0.2 | 2.1 ± 0.2 | 3.6 ± 0.6 |
| $t_{1/2}$ (hr) | 1.7 ± 0.2 | 37.2 ± 16.1 | 4.3 ± 1.3 |
| AUC (μmol · hr/L) (0-∞ h) | 9.6 ± 2.4 | 76.0 ± 31.4 | 6.4 ± 1.6 |

The results showed, unexpectedly, that IQC/Arg 250 mg reached a maximum plasma concentration ($C_{max}$) of 4.2 μM, nearly 2-fold higher than 2.2 μM shown by IQC 500 mg. It was also surprising that the area under the curve extrapolated to infinity [AUC (0-∞h)], an estimate of total drug availability, for IQC/Arg 250 mg was nearly 8-fold larger than that of IQC 500 mg, despite the fact that only half as much isoquercitrin was administered. Clearly, the data indicate a statistically significant improvement in isoquercitrin absorption when it is combined with L-arginine.

Moreover, the $C_{max}$ and AUC (0-6 h) previously reported for enzymatically modified isoquercitrin (administered at 2 mg quercetin aglycone/kg body weight) were 1.84 μM and 5.99 μmol·hr/L, respectively. See Murota et al. By contrast, the respective $C_{max}$ and AUC (0-6 h) values for IQC/Arg 250 mg (administered at 2.56 mg quercetin aglycone/kg body weight) were 3.32 μM and 9.27 μmol·hr/L, indicating greater bioavailability of isoquercetin from the IQC/Arg formulation, as compared to the enzymatically modified isoquercitrin, despite the similar doses of isoquercitrin administered.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A water-soluble pharmaceutical composition comprising isoquercitrin, L-arginine, and ascorbic acid or an alkali salt thereof, wherein a molar ratio between the isoquercitrin, L-arginine, and the alkali salt of ascorbic acid is 1:1.6-2.6: 0.16-1.95.

2. The water-soluble pharmaceutical composition of claim 1, wherein the composition includes the alkali salt of ascorbic acid, the alkali salt being a sodium salt or a potassium salt.

3. The water-soluble pharmaceutical composition of claim 2, wherein the composition is an oral formulation selected from the group consisting of a liquid, a capsule, a tablet, a pill, and a gel.

4. The water-soluble pharmaceutical composition of claim 2, wherein the composition is a topical formulation selected from the group consisting of a solution, a liniment, a lotion, a cream, an ointment, a paste, a gel, and an emulgel.

5. The water-soluble pharmaceutical composition of claim 1, further comprising vitamin B1, vitamin B3, vitamin B6, vitamin B9, or vitamin B12.

6. The water-soluble pharmaceutical composition of claim 5, wherein the composition is an oral formulation selected from the group consisting of a liquid, a capsule, a tablet, a pill, and a gel.

7. The water-soluble pharmaceutical composition of claim 5, wherein the composition is a topical formulation selected from the group consisting of a solution, a liniment, a lotion, a cream, an ointment, a paste, a gel, and an emulgel.

8. The water-soluble pharmaceutical composition of claim 2, further comprising vitamin B1, vitamin B3, vitamin B6, vitamin B9, or vitamin B12.

9. The water-soluble pharmaceutical composition of claim 8, wherein the composition is an oral formulation selected from the group consisting of a liquid, a capsule, a tablet, a pill, and a gel.

10. The water-soluble pharmaceutical composition of claim 8, wherein the composition is a topical formulation selected from the group consisting of a solution, a liniment, a lotion, a cream, an ointment, a paste, a gel, and an emulgel.

11. The water-soluble pharmaceutical composition of claim 1, wherein the molar ratio between the isoquercitrin, L-arginine, and the alkali salt of ascorbic acid is 1:1.8-2.5: 0.36-1.25.

12. The water-soluble pharmaceutical composition of claim 11, wherein the alkali salt of ascorbic acid is a sodium salt or a potassium salt.

13. The water-soluble pharmaceutical composition of claim 12, wherein the composition is an oral formulation selected from the group consisting of a liquid, a capsule, a tablet, a pill, and a gel.

14. The water-soluble pharmaceutical composition of claim 12, wherein the composition is a topical formulation selected from the group consisting of a solution, a liniment, a lotion, a cream, an ointment, a paste, a gel, and an emulgel.

15. The water-soluble pharmaceutical composition of claim 11, further comprising vitamin B1, vitamin B3, vitamin B6, vitamin B9, or vitamin B12.

16. The water-soluble pharmaceutical composition of claim 15, wherein the composition is an oral formulation selected from the group consisting of a liquid, a capsule, a tablet, a pill, and a gel.

17. The water-soluble pharmaceutical composition of claim 15, wherein the composition is a topical formulation selected from the group consisting of a solution, a liniment, a lotion, a cream, an ointment, a paste, a gel, and an emulgel.

18. The water-soluble pharmaceutical composition of claim 12, further comprising vitamin B1, vitamin B3, vitamin B6, vitamin B9, or vitamin B12.

19. The water-soluble pharmaceutical composition of claim 18, wherein the composition is an oral formulation selected from the group consisting of a liquid, a capsule, a tablet, a pill, and a gel.

20. The water-soluble pharmaceutical composition of claim 18, wherein the composition is a topical formulation selected from the group consisting of a solution, a liniment, a lotion, a cream, an ointment, a paste, a gel, and an emulgel.

\* \* \* \* \*